(12) United States Patent
Hendriks et al.

(10) Patent No.: US 9,999,739 B2
(45) Date of Patent: Jun. 19, 2018

(54) PATIENT INTERFACE DEVICE HAVING AN ENGINEERED SURFACE FOR PROVIDING LOW FRICTION AND IMPROVED COMFORT TO THE USER

(71) Applicant: KONINKLIJKE PHILIPS N.V., Eindhoven (NL)

(72) Inventors: Cornelis Petrus Hendriks, Eindhoven (NL); Rudolf Maria Jozef Voncken, Eindhoven (NL); Willem Potze, Geldrop (NL); Nicolaas Petrus Willard, Valkenswaard (NL); Joyce Van Zanten, Waalre (NL); Mareike Klee, Straelen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 822 days.

(21) Appl. No.: 14/370,982

(22) PCT Filed: Jan. 10, 2013

(86) PCT No.: PCT/IB2013/050229
§ 371 (c)(1),
(2) Date: Jul. 8, 2014

(87) PCT Pub. No.: WO2013/108160
PCT Pub. Date: Jul. 25, 2013

(65) Prior Publication Data
US 2015/0013682 A1    Jan. 15, 2015

Related U.S. Application Data

(60) Provisional application No. 61/586,869, filed on Jan. 16, 2012.

(51) Int. Cl.
*A61M 16/06* (2006.01)
*A61M 16/08* (2006.01)
*A61M 16/20* (2006.01)

(52) U.S. Cl.
CPC ........ *A61M 16/0605* (2014.02); *A61M 16/06* (2013.01); *A61M 16/0622* (2014.02);
(Continued)

(58) Field of Classification Search
CPC .......... A61M 16/0605; A61M 16/0622; A61M 16/0633; A61M 16/0644; A61M 16/06;
(Continued)

(56) References Cited

U.S. PATENT DOCUMENTS 5,753,343 A    5/1998  Braun et al.
6,851,425 B2   2/2005  Jaffre et al.
(Continued)

FOREIGN PATENT DOCUMENTS

WO    2009026627 A1    3/2009
WO    2011014931 A1    2/2011
WO    2011/121525     10/2011

*Primary Examiner* — Todd J Scherbel
*Assistant Examiner* — Elliot S Ruddie

(57) ABSTRACT

A patient interface device includes an elastomeric contacting portion that is structured to directly engage the skin of the user. The contacting portion has an engineered surface that includes a plurality of non-random, predesigned surface features designed to reduce friction and improve user comfort. In one implementation, the pitch between each immediately adjacent pair of the surface features is less than or equal to a predetermined maximum pitch value, and the height of each of the surface features is less than or equal to a predetermined maximum height value.

20 Claims, 11 Drawing Sheets

(52) U.S. Cl.
CPC .... *A61M 16/0633* (2014.02); *A61M 16/0644* (2014.02); *A61M 16/0666* (2013.01); *A61M 16/0683* (2013.01); *A61M 16/0816* (2013.01); *A61M 16/208* (2013.01); *A61M 2016/0661* (2013.01); *A61M 2205/02* (2013.01); *A61M 2207/00* (2013.01); *Y10T 29/49* (2015.01)

(58) Field of Classification Search
CPC .......... A61M 16/0666; A61M 16/0683; A61M 16/0816; A61M 16/208; A61M 2016/0661; A61M 2205/02; A61M 2205/0216; A61M 2207/00; A61M 2205/0222; A61M 1/06; A61M 1/066; Y10T 29/49; Y10T 428/24479; Y10T 428/24612; B32B 3/30; H04R 1/10; H04R 1/12; B44C 1/005; A61J 9/06; A61J 9/0623; A61J 17/00; A61J 17/02; A61J 17/008; A61J 11/00; A61J 11/0035; A61J 11/005; A61J 11/0045; A61J 11/0055; A61J 13/00; A61J 9/00; A61B 5/681

USPC .......... 128/200.24, 206.28, 205.25, 204.18, 128/205.11, 205.27, 206.12, 206.19, 128/206.21, 206.24, 206.26, 207.11, 128/207.12, 207.17; 428/903
See application file for complete search history.

(56) References Cited

U.S. PATENT DOCUMENTS

| | | |
|---|---|---|
| 7,069,932 B2 | 7/2006 | Eaton et al. |
| 7,640,933 B1 | 1/2010 | Ho |
| 2002/0026943 A1 | 3/2002 | Castiglione |
| 2010/0018534 A1 | 1/2010 | Veliss et al. |
| 2010/0065059 A1 | 3/2010 | Ho |
| 2011/0023882 A1* | 2/2011 | Nickol .................. A61M 16/06 128/206.24 |
| 2011/0088699 A1 | 4/2011 | Skipper et al. |
| 2011/0146684 A1 | 6/2011 | Wells et al. |
| 2012/0202009 A1* | 8/2012 | Motofuji ............. B29C 33/3857 428/156 |
| 2014/0238407 A1 | 8/2014 | Ho |

* cited by examiner

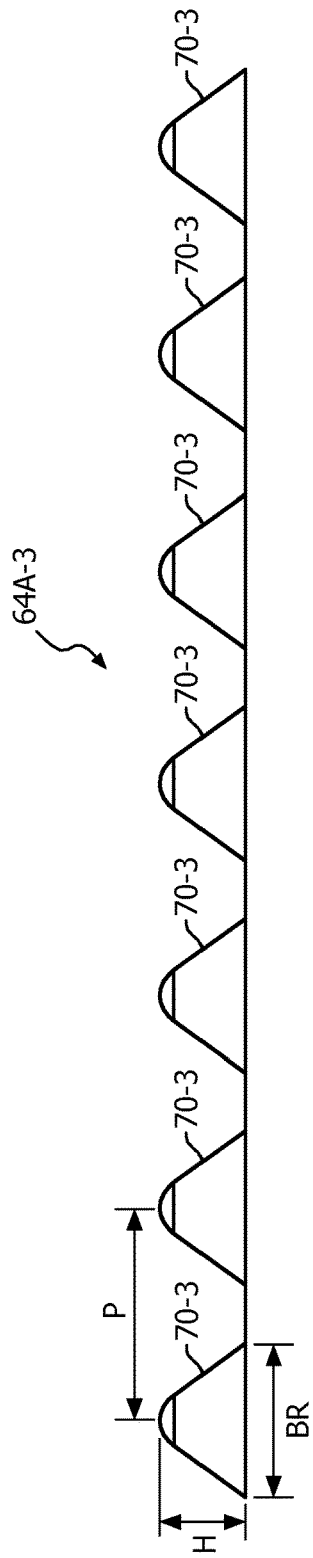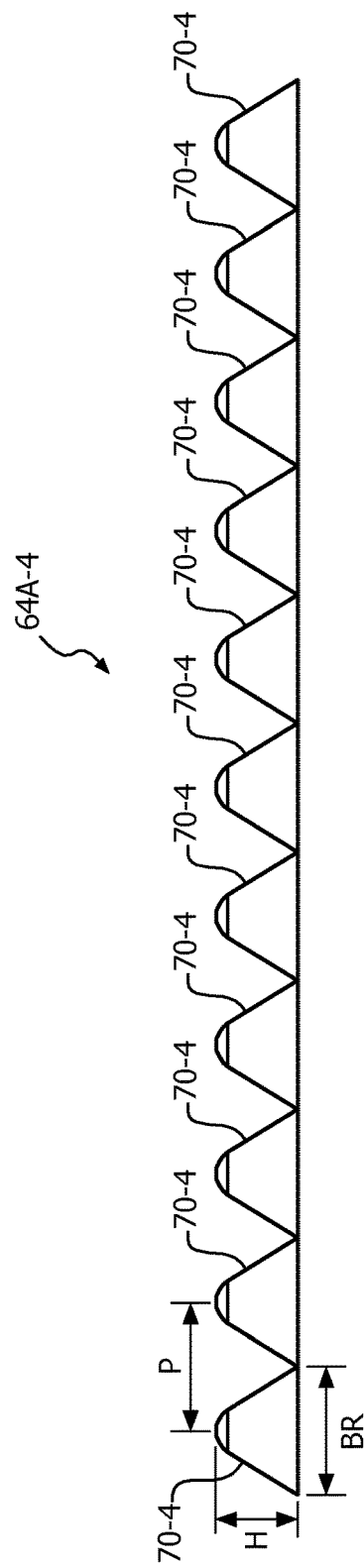
FIG. 8
FIG. 9

PATIENT INTERFACE DEVICE HAVING AN ENGINEERED SURFACE FOR PROVIDING LOW FRICTION AND IMPROVED COMFORT TO THE USER

CROSS REFERENCE TO RELATED APPLICATIONS

This application is a national filing of PCT application Serial No. PCT/IB2013/050229, filed Jan. 10, 2013, published as WO 2013/108160 A1 on Jul. 25, 2013, which claims the benefit of U.S. provisional application Ser. No. 61/586,869 filed Jan. 16, 2012, which is incorporated herein by reference.

BACKGROUND OF THE INVENTION

1. Field of the Invention

The present invention pertains to respiratory masks, also commonly referred to as patient interface devices, that are used to deliver a breathing gas to the user, and, in particular, to an engineered surface for such a device that is structured to contact the skin of the user and provide low friction and improved comfort for the user.

2. Description of the Related Art

A variety of respiratory masks are known that have flexible seals and cover the nose, mouth, or both of a human user. The seals, which are also commonly referred to as cushions, are intended to create a seal against the user's face. Because of the sealing effect that is created, gases can be provided at a positive pressure within the mask for delivery to the airway of the user.

The uses for such masks range from high altitude breathing, i.e., aviation applications, to mining and fire fighting applications, to various medical diagnostic and therapeutic applications. For example, such masks are used in the delivery of continuous positive airway pressure (CPAP) or variable airway pressure, such as a bi-level pressure that varies with the user's respiratory cycle or an auto-titrating pressure that varies with the monitored condition of the user. Typical pressure support therapies are provided to treat a medical disorder, such as sleep apnea syndrome, in particular, obstructive sleep apnea (OSA), or congestive heart failure. During use, such respiratory masks, also often referred to as patient interface devices, are strapped on the head of the patient in order to interface the pressure generating device (e.g., a CPAP machine) with the patient.

A requisite of such respiratory masks is that they provide an effective seal against the user's face to prevent leakage of the gas being supplied, while also providing a comfortable user/seal interface. This problem is most crucial because such masks are typically worn for an extended period of time. One concern in such a situation is that a user may avoid wearing an uncomfortable mask, defeating the purpose of the prescribed pressure support therapy.

Surveys have shown that as much as 70% of the population of users of respiratory masks suffers from facial red marks in some form after using a respiratory mask during therapy. The recovery time varies from minutes to hours, but in extreme cases, longer-lasting skin damage and pressure-sores can occur. The root causes of red mark formation are the prolonged pressure and shear loading of the skin by the mask cushion in combination with the build-up of moisture and heat in the skin due to the prolonged occlusion. An important factor in these root causes is skin friction.

Thus, there is a need for a surface for use in a device, such as a respiratory mask, that is structured to contact the skin of the user for prolonged periods that provides reduced friction and/or increased comfort for the user.

SUMMARY OF THE INVENTION

Accordingly, it is an object of the present invention to provide a patient interface device that has a surface that is structured to contact the skin of the user that overcomes the shortcomings of conventional patient interface devices by providing reduced friction and/or improved user comfort.

It is yet another object of the present invention to provide a method of making patient interface device that has a surface that is structured to contact the skin of the user that does not suffer from the disadvantages associated with conventional design and manufacturing techniques.

In one embodiment, a patient interface device is provided that includes a contacting portion structured to directly engage the user's skin. At least a section of contacting portion has an engineered surface including a plurality of non-random, predesigned surface features each having a similar geometry, wherein in the section the pitch between each immediately adjacent pair of the surface features is less than or equal to a predetermined maximum pitch value, and wherein in the section the height of each of the surface features is less than or equal to a predetermined maximum height value.

In another embodiment, a method of making a patient interface device is provided. The method includes designing an engineered surface wherein at least a section of the engineered surface comprises a plurality of non-random, predesigned surface features each having a similar geometry, wherein in the section a pitch between each immediately adjacent pair of the surface features is less than or equal to a predetermined maximum pitch value, and wherein in the section a height of each of the surface features is less than or equal to a predetermined maximum height value, and forming a contacting portion for the patient interface device in a manner wherein the contacting portion includes the engineered surface, the contacting portion being structured to directly engage the skin of the user.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIGS. 6-9 are cross sectional views of the contacting portion of FIG. 4 according to various particular alternative implementations.

DETAILED DESCRIPTION OF EXEMPLARY EMBODIMENTS

Figure 1:
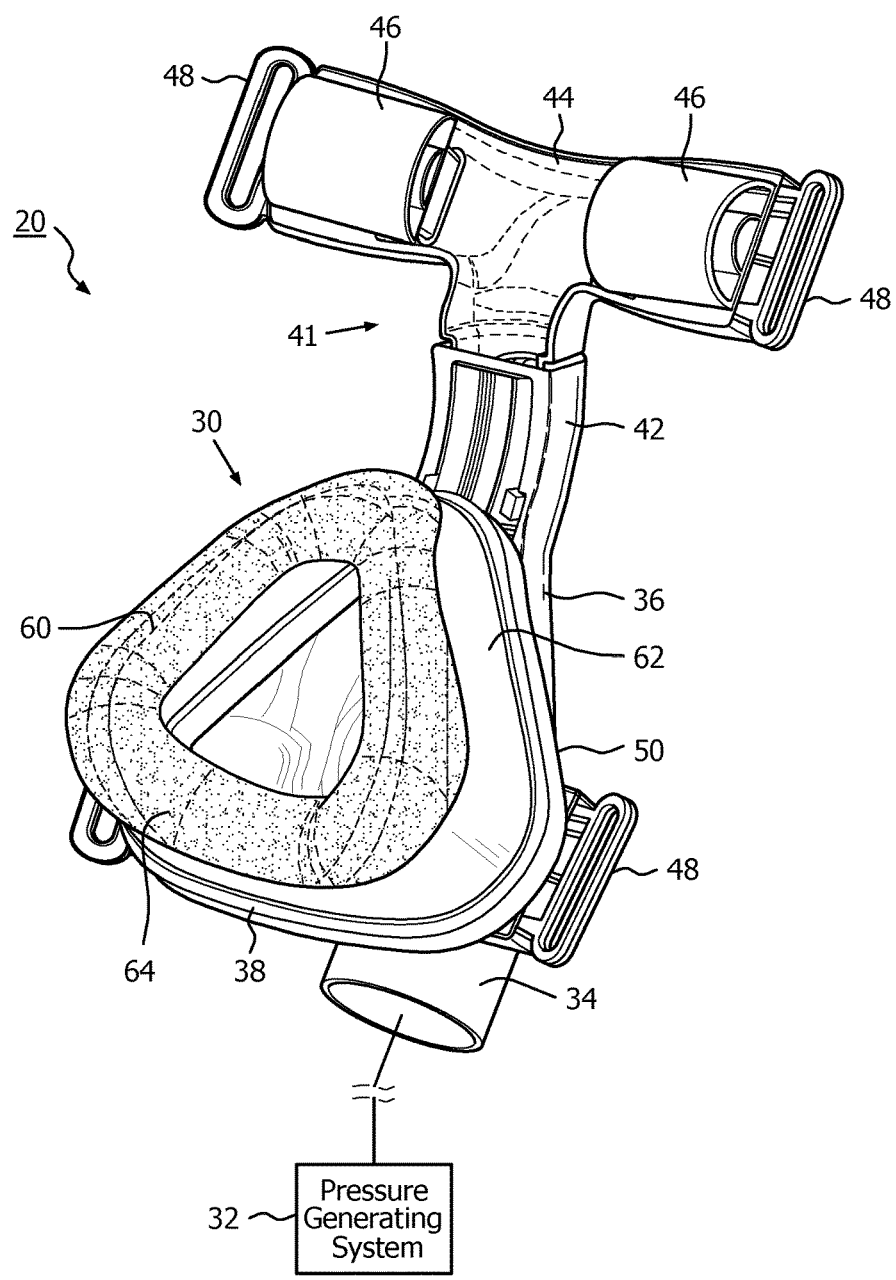
FIGS. 1 and 2 are isometric and side elevational views, respectively, of a system adapted to provide a regimen of respiratory therapy to a patient according to one exemplary embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 2:
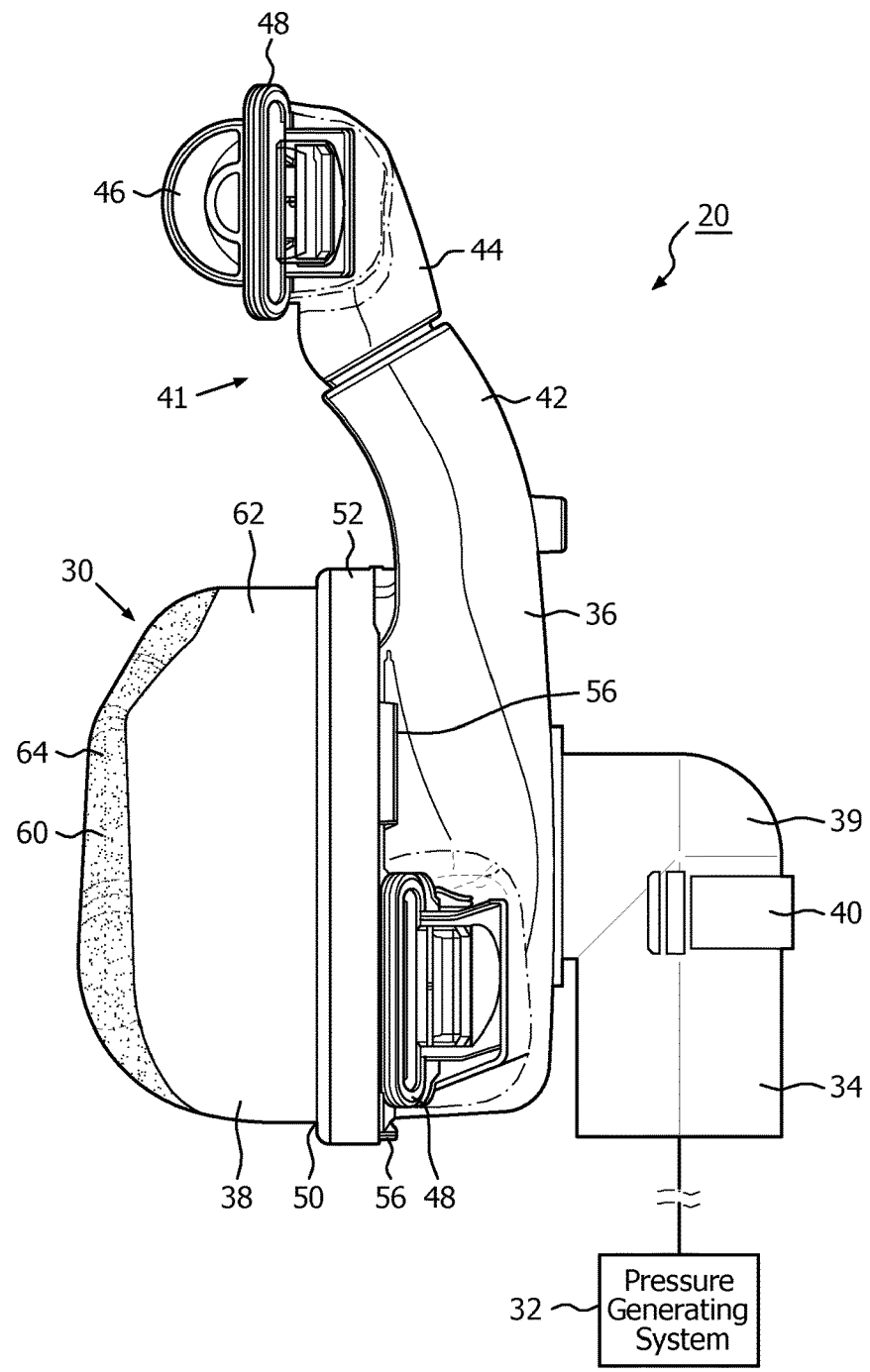

FIGS. 1 and 2 are isometric and side elevational views, respectively, of a system 20 adapted to provide a regimen of respiratory therapy to a patient according to one exemplary embodiment of the present invention. As seen in FIGS. 1 and 2, system 20 includes a respiratory mask 30 (also referred to as a patient interface device) according to one exemplary embodiment that is shown schematically attached to a pressure generating system 32 via a user circuit 34, as is conventionally known in the art. Pressure generating system 32 is any device capable of generating a flow of breathing gas or providing gas at an elevated pressure. Examples of such pressure generating systems include ventilators, constant pressure support devices (such as a continuous positive airway pressure device, or CPAP device) in which the pressure provided to the user is constant over the user's respiratory cycle, and variable pressure devices (e.g., BiPAP®, Bi-Flex®, or C-Flex™ devices manufactured and distributed by Philips Respironics of Murrysville, Pa.) in which the pressure provided to the user varies with the user's respiratory cycle, and auto-titration pressure support devices.

Respiratory mask 30 includes a shell 36 and a seal 38 attached to shell 36. User circuit 34 is coupled to a port defined in a first side of shell 36 and, in the illustrated embodiment, includes an elbow connector 39 for that purpose. In the exemplary embodiment, user circuit 34 is connected to shell 36 so as to pivot or rotate relative to the shell 36 and may or may not be detachable therefrom. In short, any suitable coupling technique for joining user circuit 34 to shell 36 is contemplated by the present invention.

In the illustrated exemplary embodiment, an exhaust vent 40 is provided in elbow connector 39 for exhausting a flow of gas from mask 30 to ambient atmosphere. Such exhaust vents are conventionally used in pressure support systems that use a single-limb, i.e., a single conduit, to communicate a flow of gas to an airway of a user. Thus, the present invention contemplates that exhaust vent 40 can be any suitable exhaust vent, and can be located not only on elbow connector 39, but alternatively on mask 30, such as on the shell 36. The particular exhaust vent 40 shown in FIG. 2 corresponds to that described in U.S. Pat. No. 6,851,425, entitled "Exhaust Port Assembly for a Pressure Support System" and owned by the assignee of the present invention.

Respiratory mask 30 can have any one of a number of different configurations, shapes, and sizes. In the illustrated, exemplary embodiment, respiratory mask 30 is a nasal mask structured to cover the nose of the patient wherein shell 36 corresponds to that described in U.S. Pat. No. 7,069,932, entitled "User Interface With Forehead Support System" and owned by the assignee of the present invention. However, other types of respiratory masks, such as, without limitation, a nasaloral mask, a nasal cushion or a full face mask, which facilitate the delivery of the flow of breathing gas to the airway of a patient, may be substituted for respiratory mask 30 while remaining within the scope of the present invention. Shell 36 is, in the exemplary embodiment, formed from a rigid or semi-rigid material, such as a polycarbonate or an injection molded thermoplastic. In addition, as seen in FIGS. 1 and 2, respiratory mask 30 includes an adjustable forehead support 41. The forehead support is generally T-shaped and includes a support arm 42 which is slideably connected to a forehead support bracket 44. Forehead support bracket 44 includes a forehead pad 46 disposed on the user contacting side to engage the forehead of the user. It is to be understood that the present invention contemplates that forehead support 41, and its individual components, can have any one of a variety of alternative configurations. The present invention also contemplates that forehead support 41 can be eliminated entirely.

In the illustrated, exemplary embodiment, a headgear (not shown) attaches to respiratory mask 30 via headgear clips 48. Headgear clips 48 attach to straps of the headgear, for example by inserting the straps into slots provided in clips 48. Clips 48 are selectively attachable to shell 36 in any suitable manner. In the illustrated embodiment, clips 48 attach to each side of forehead support bracket 44 and to each side of the lower portion of shell 36. It can thus be appreciated that the headgear and clip 48 can have any configuration so as to be selectively attachable to respiratory mask 30. It is to be further understood that the present invention contemplates eliminating all, or a portion, of clips 48 and attaching the headgear straps to directly the shell 36.

Seal 38, also referred to as a cushion, is, in the exemplary embodiment, a unitary structure made of a soft, flexible, cushiony, elastomeric material, such as, without limitation, silicone, an appropriately soft thermoplastic elastomer (such as thermoplastic polyurethanes (TPU)), latex, polybutadiene, a closed cell foam, or any combination of such materials, and includes a first end portion 50 that couples to shell 36. In the illustrated embodiment, first end portion 50 is generally triangular-shaped and attaches to similarly-shaped opening provided in a second side of shell 36. In the illustrated embodiment, shell 36 and first end portion 50 of seal 38 that attaches thereto are both generally planer, i.e., both line in a linear plane. Alternatively, it should be noted that the present invention contemplates that shell 36 and first end portion 50 can be contoured, when viewed in profile, so that first end portion 50, for example, does not lie in a common plane with shell 36. It is to be further understood that the present invention contemplates using any suitable technique for attaching first end portion 50 of seal 38 to shell 36. Such techniques may include permanently bonding seal 38 to shell 36, for example using adhesives or molding seal 38 onto shell 36, or attaching seal 38 to shell 36 using mechanical fasteners in a manner wherein seal 38 is selectively detachable from shell 36.

In the illustrated embodiment, a lock ring 52 slips over seal 38 and engages a lip defined on first end portion 50 of seal 38. Lock ring 52 attaches to shell 36 in any suitable manner. For example, the present invention contemplates providing locking tabs 56 on lock ring 52 that selectively attach to engaging portions of shell 36. When coupled to shell 36, seal 38 defines a chamber for receiving the nose of the user when respiratory mask 30 is donned by the user so that the user's airway is in fluid communication with the chamber.

Seal 38 also includes a second end portion 60 for sealing engagement with the face of a user, and a sidewall 62 extending between first end portion 50 and second end portion 62. According to the principles of the present invention, at least a portion of the exposed surface of seal 38 at second end portion 60 includes a contacting portion 64 that comprises an engineered surface structured to contact the skin of the user. In one embodiment, contacting portion 64 covers the entire exposed surface of seal 38. In an alternative embodiment, contacting portion 64 covers only selected, well defined areas of seal 38 where red mark formation is strongly present (e.g., the nose bridge region). This embodiment may, for example, be employed in cases where a low friction surface that covers the entire exposed surface of seal 38 would cause macro-slip of seal 38, and thereby cause mask instability or leakage. In the illustrated, exemplary embodiment shown in FIGS. 1 and 2, which, as described elsewhere herein, is a nasal mask, contacting portion 64 is structured to contact the area of the user generally around the nose including over the bridge of the nose.

As noted above, contacting portion 64 comprises an engineered surface. As used herein, the term "engineered surface" shall mean a designed surface texture having a plurality of one or more types of surface features wherein for each type of surface feature the surface feature has a non-random, predefined/predesigned geometry and/or non-random, predefined/predesigned dimensions and/or interrelationships among one another. The surface features that may form part of an engineered surface include, for example and without limitation, bumps, dimples, pillars, domes, valleys, ridges, undulations and serrations. These surface features minimize the real area of contact with the skin, thereby providing low friction (compared to a nominally flat surface). In one particular exemplary embodiment, the surface features that may form part of an engineered surface are "non-connected surface features". As used herein, the term "non-connected surface feature" shall mean a surface feature that extends upwardly from a surface and that is not connected to any adjacent surface features at a point located above the surface from which the surface feature extends by, for example, a ridge or similar connecting structure. Examples of such "non-connected surface features" are the domes shown in FIG. 3A and the pillars shown in FIG. 3C and described below.

Example engineered surfaces including dome-shaped structures and serrated configurations are described in detail elsewhere herein (FIGS. 3A-3C and 3G-3J). Contacting portion 64 comprising an engineered surface in the various embodiments described herein is advantageous as it reduces the likelihood of red marks being formed on the user's skin during use and/or improves user comfort by reducing skin friction (which reduces skin shear loading and normal pressure peaks), providing a soft silky feel, and/or providing self cleaning properties for seal 38 (described in greater detail elsewhere herein).

Figure 3A:
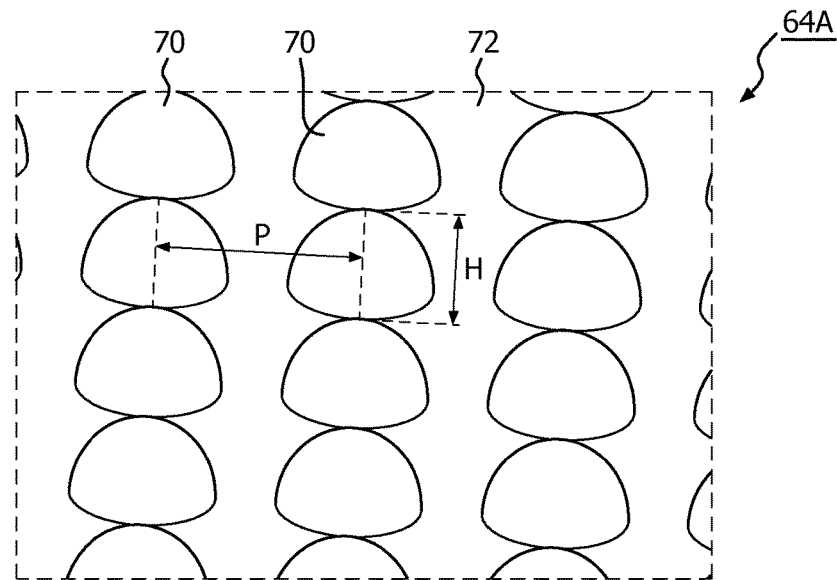
FIGS. 3A-3J are schematic isometric views of exemplary embodiments of contacting portions each having an engineered surface that may be employed in the respiratory mask of the system of FIGS. 1 and 2.
Figure 3B:
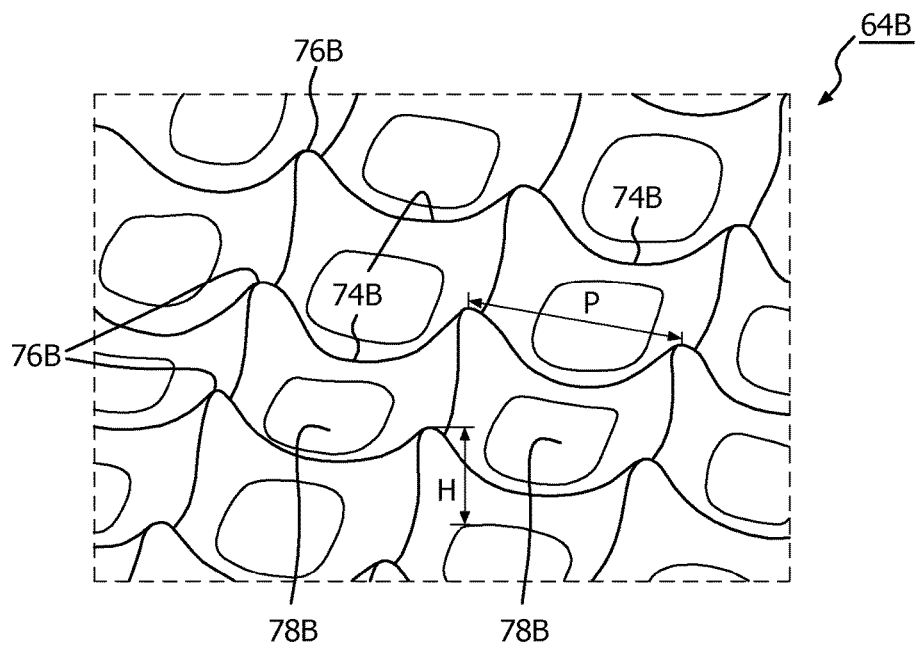
Figure 3C:
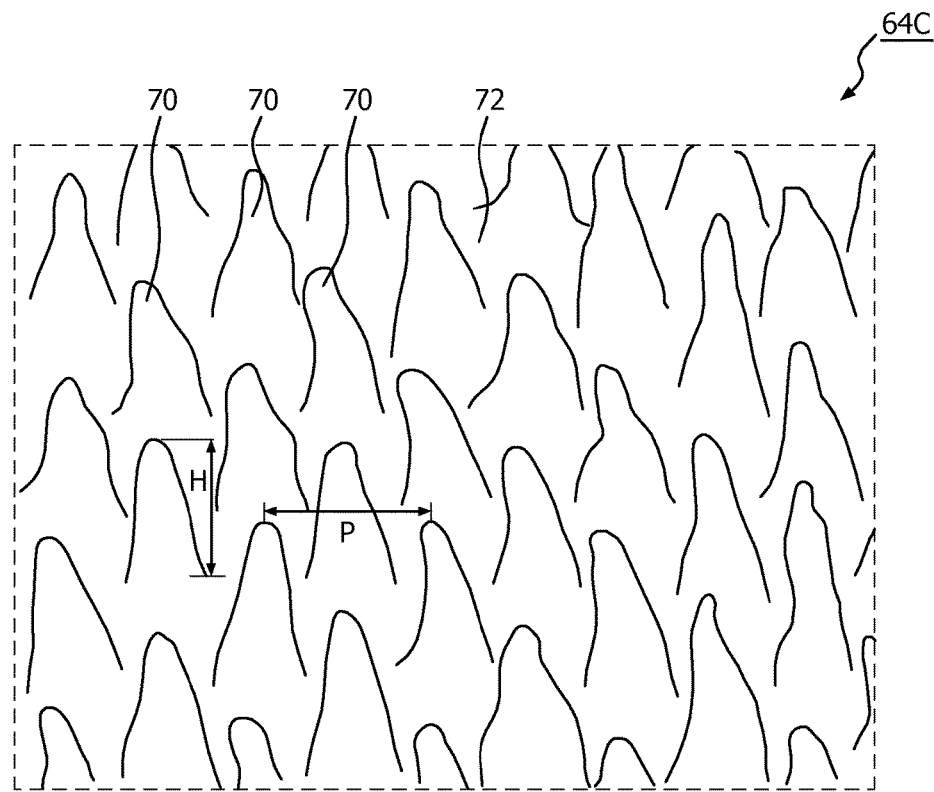

The particular engineered surface of contacting portion 64 may have any of a number of different configurations within the scope of the present invention. Three exemplary contacting portions 64A through 64C, each having a different exemplary engineered surface, are shown in FIGS. 3A through 3C, respectively. Each contacting portion 64A-64C (and thus each exemplary engineered surface thereof) represents a particular, non-limiting exemplary embodiment that may be employed in respiratory mask 30.

As seen in FIG. 3A, the engineered surface of contacting portion 64A includes a number of surface features 70, wherein each surface feature 70 is a dome-shaped structure extending upwardly from a bottom surface 72 of contacting portion 64A. As seen in FIG. 3B, the engineered surface of contacting portion 64B comprises a serrated configuration wherein the surface features include a number of ridges 74B and a number of pillar members 76B formed by the intersection of four adjacent ridges 74B. In addition, as seen in FIG. 3B, a valley 78B is formed in the area defined by each group of four immediately adjacent ridges 74B. As seen in FIG. 3C, the engineered surface of contacting portion 64C includes a number of surface features 70 wherein each surface feature 70 is a pillar structure extending upwardly from a bottom surface 72 of contacting portion 64C. Still further exemplary contacting portions 64G-64J comprising further exemplary engineered surfaces are shown in FIGS. 3G-3J.

Furthermore, in one exemplary embodiment of the present invention, the engineered surface of contacting portion 64 is characterized by two particular design parameters, namely the pitch (P) of the surface features and the height (H) of the surface features. As used herein, the term "pitch" shall mean the distance between corresponding portions of immediately adjacent pairs of like surface features, and the term "height" shall mean the vertical distance between the highest point of a surface feature and the lowest surface 72 of contacting portion 64 on which the surface features sits. Referring to FIG. 3A, the pitch (P) and the height (H) of the dome-shaped surface features 70 of that embodiment are labeled P and H, respectively. Referring to FIG. 3B, in the serrated configuration of those embodiments, pitch is measured between immediately adjacent pillar members 76B and height is measured from the top of each pillar member 76B (which are the tallest surface features) to the deepest point of the valleys 78B. Alternatively, pitch may be measured between the centers of immediately adjacent ridges 74B.

As noted elsewhere herein, seal 38 is, in the exemplary embodiment, made of a soft, flexible, cushiony, elastomeric material. In one exemplary, non limiting embodiment, the specific material may be silicone having a durometer of 40 Shore A. In another exemplary, non limiting embodiment, the specific material may be liquid silicone rubber having a durometer of 5 Shore A. Furthermore, through testing and modeling (e.g., FEM modeling using numerical simulations) of the various embodiments of contacting portion 64 described herein (with the criteria being low friction and skin comfort), the present inventors have determined that the performance of contacting portion 64 may be optimized by employing an engineered surface wherein the pitch between each immediately adjacent pair of like surface features is less than or equal to some predetermined maximum pitch value ($P_{max}$) and the height of each like surface feature is less than or equal to some predetermined height value ($H_{max}$).

Figure 4:
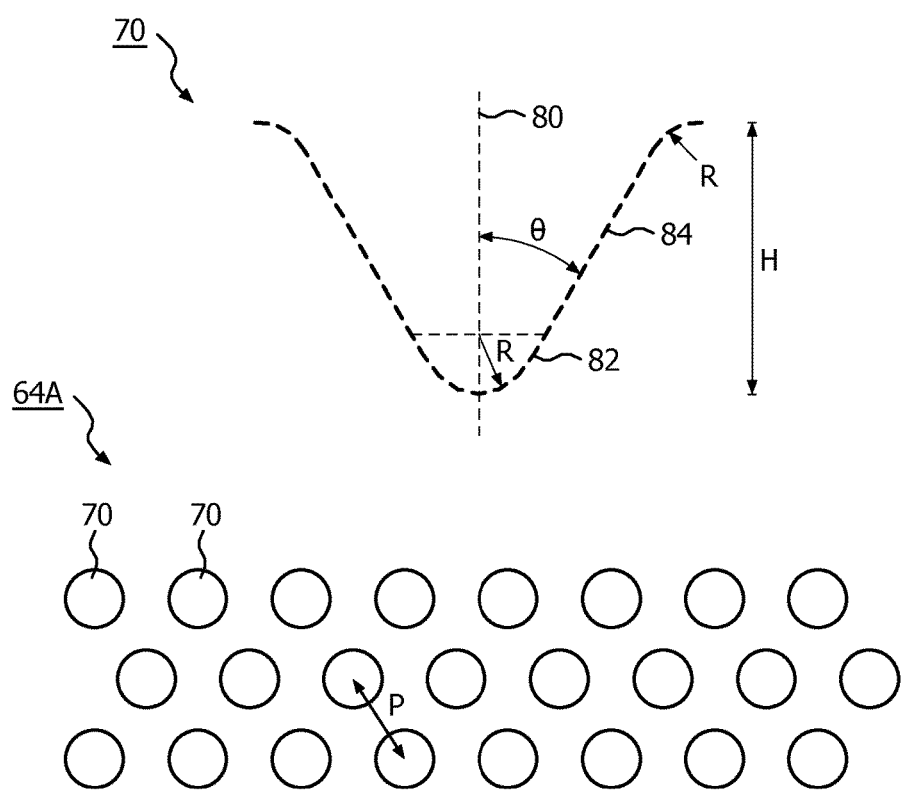
FIG. 4 is a schematic representation of the contacting portion of FIG. 3A according to one particular exemplary embodiment.

In one particular embodiment, the engineered surface is characterized by a pitch wherein the pitch is consistent and equal throughout the surface (as used herein, when comparing the pitch values of adjacent surface features within an engineered surface, "equal" shall mean the pitch values are all within a 10% or less manufacturing tolerance of one another) and is less than or equal to $P_{max}$. Examples of such surfaces wherein the pitch is consistent and equal are shown in FIGS. 3A, 3B and FIG. 4 (described below).

Figure 3D:
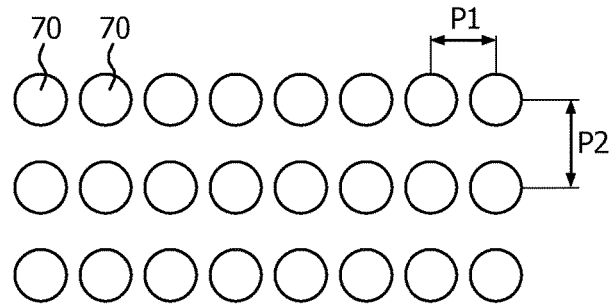
Figure 3E:
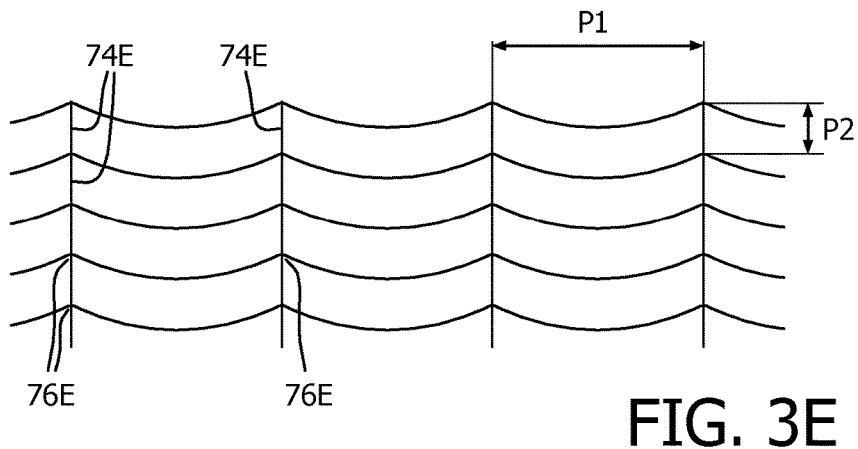

In an alternative particular embodiment, the engineered surface is characterized by a pitch wherein the pitch is anisotropic, meaning it has different dimensions/properties along different directions. More particularly, in this embodiment, the pitch will have a consistent and equal first pitch value P1 in a first direction and a consistent and equal second pitch value P2 in second direction transverse to (e.g., perpendicular to) the first direction. One example of such an embodiment is shown in FIG. 3D using dome-shaped surface features 70. Another example of such an embodiment is shown in FIG. 3E, wherein a serrated configuration as described elsewhere herein is employed.

Figure 3F:
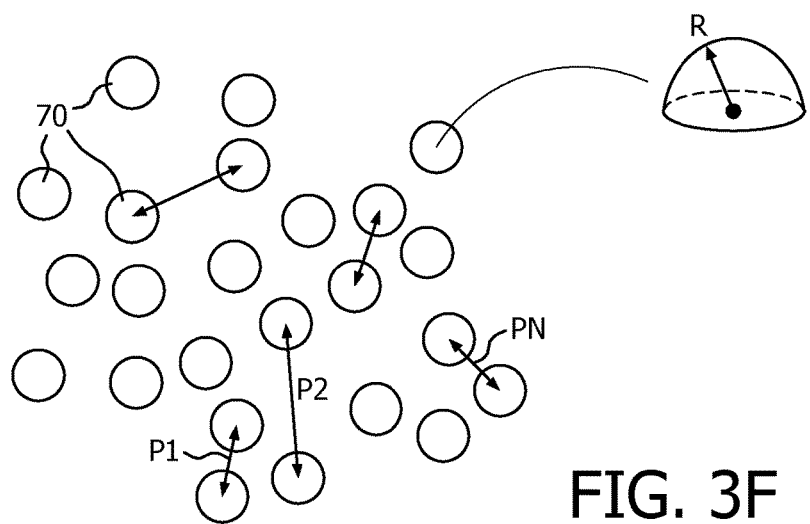
Figure 3G:
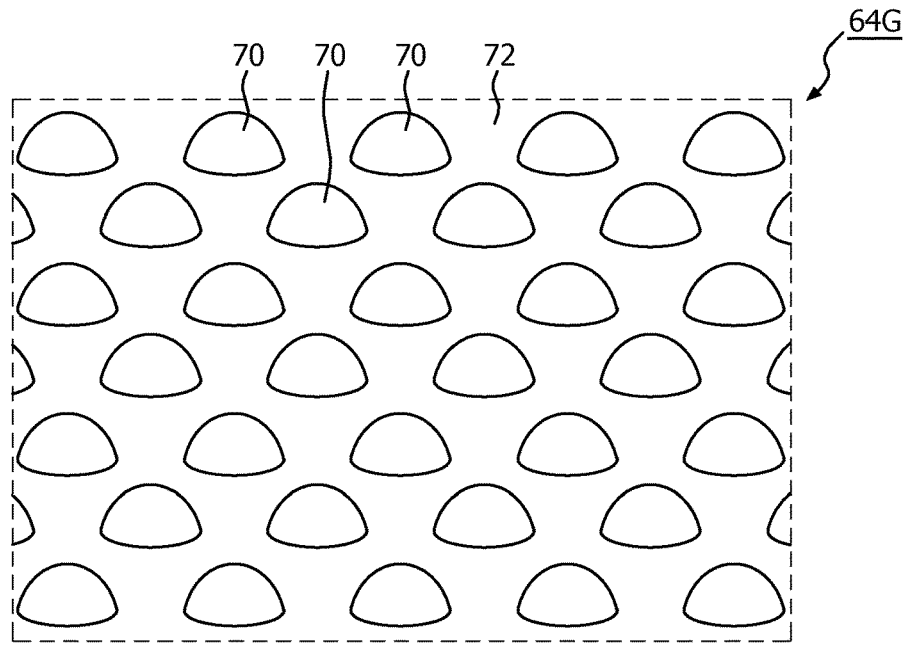
Figure 3H:
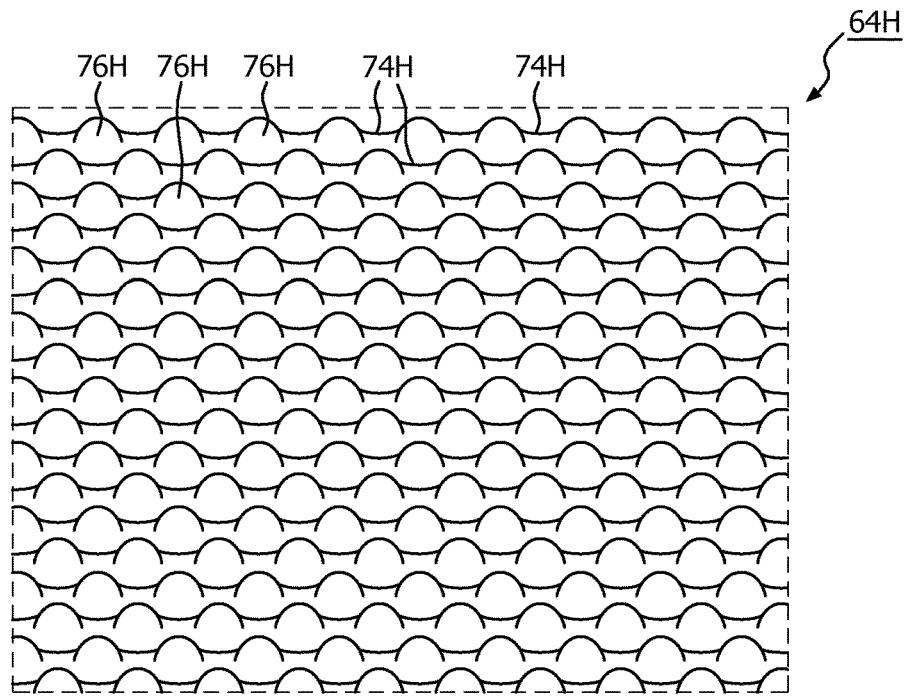
Figure 3I:
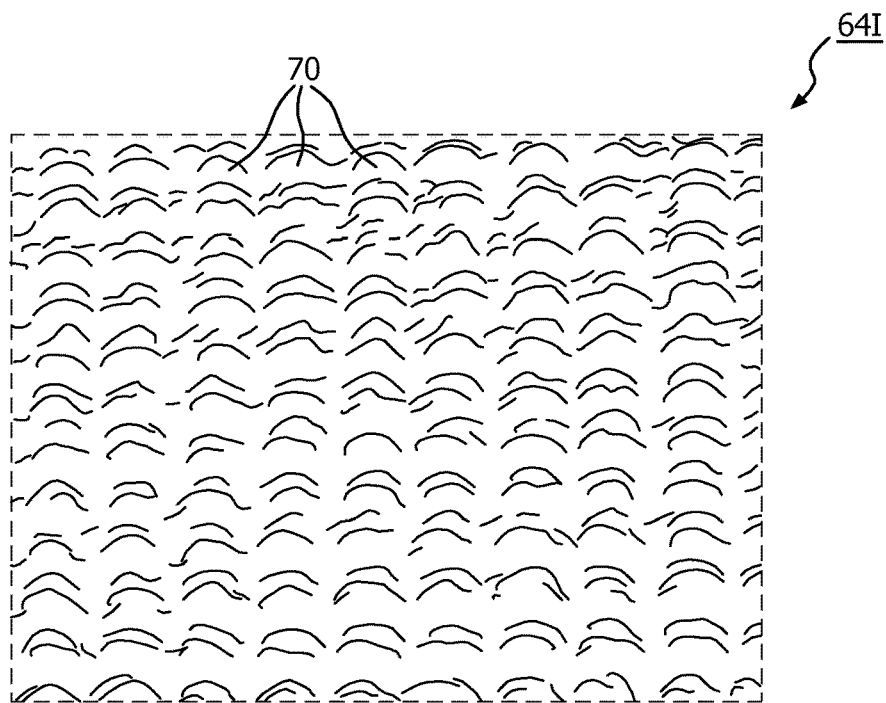
Figure 3J:
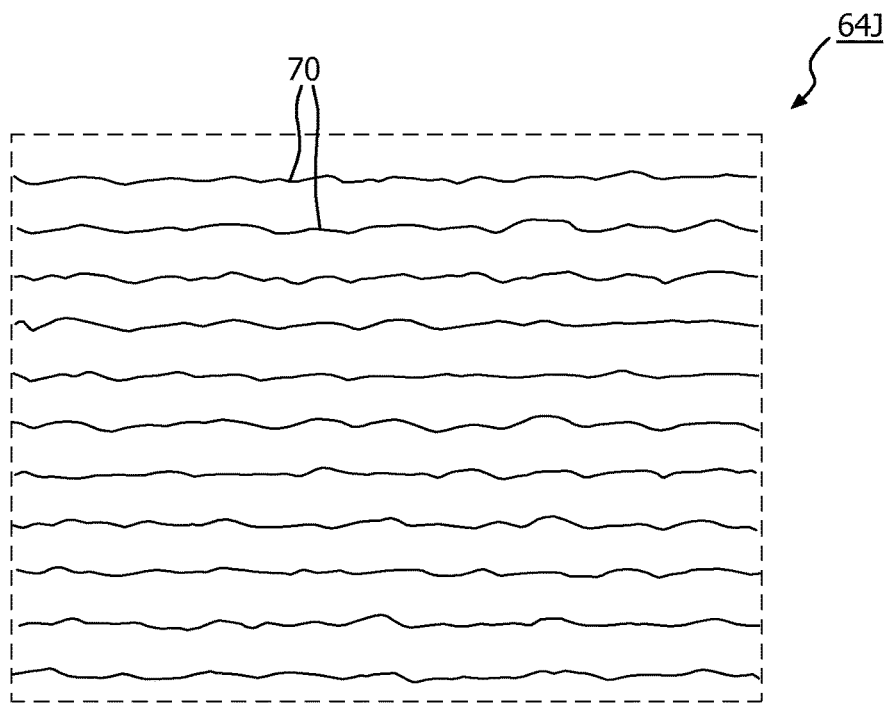

In another alternative particular embodiment, the engineered surface is characterized by a pitch wherein the pitch may vary throughout the surface but in each case is less than or equal to $P_{max}$. An example of such an embodiment is shown in FIG. 3F using dome-shaped surface features 70 (although features having other shapes may also be employed). In the illustrated embodiment, Pi=P1, P2, . . . PN, wherein $0 < Pi \leq P_{max}$, or $2R < Pi \leq P_{max}$, where R is the radius of the hemispherically-shaped dome. In one particular embodiment, each of the pitch values is within 50% of one another. In another particular embodiment, the maximum variation of the pitch values is somewhere between 10% and 50% of one another (to avoid optical stitching and vibration noise effects).

Similarly, in another particular embodiment, the engineered surface is characterized by a height wherein the height is consistent and equal throughout the surface (i.e., for each similar surface feature; as used herein, when comparing the height values of the surface features within an engineered surface, "equal" shall mean within a 30% or less manufacturing tolerance of one another) and is less than or equal to $H_{max}$.

Moreover, in one particular, non limiting exemplary embodiment, $P_{max}$ is equal to 100 microns and $H_{max}$ is equal to 100 microns. In other words, in this exemplary embodiment, pitch P and height H are characterized as follows: P≤100 microns and H≤100 microns. In another particular, non limiting exemplary embodiment which is a refinement of the embodiment just described, pitch P and height H are characterized as follows: P≤50 microns (or, alternatively P≤100 microns, or 20 microns≤P≤50 microns) and 10 microns≤H≤40 microns. In still a further particular, non limiting exemplary embodiment which is also a further refinement of the embodiment just described, pitch P and height H are characterized as follows: 20 microns≤P≤50 microns (or, alternatively 10 microns≤P≤50 microns, P≤50 microns, or P≤100 microns) and 10 microns≤H≤20 microns. In still a further non-limiting, exemplary embodiment, $P_{max}$ is greater than or equal to 10 microns and less than or equal to 100 microns and $H_{max}$ is greater than or equal to 10 microns and less than or equal to 100 micron. These exemplary embodiments may be implemented in, for example, any of the engineered surface configurations shown in FIGS. 3A-3C and described elsewhere herein. Through testing and modeling, the present inventors have determined that an engineered surface according to these exemplary embodiments, when implemented on a skin contacting surface such as contacting portion 64, will not have a negative effect on the user's skin during use and thus will optimize performance. For example, it has been determined that such configurations will not provide an undue stress concentration on the deeper layers of the user's skin.

Thus, based on the above, the following exemplary, non-limiting combinations of pitch and height in an engineered surface are possible:

TABLE 1

| Pitch | Height |
|---|---|
| $P_{max}$ = 100 microns | (i) $H_{max}$ = 100 microns, or (ii) $H_{max}$ = 40 microns, or (iii) $H_{max}$ = 20 microns, or (iv) $H_{max}$ ≥ 10 microns and ≤100 microns |
| $P_{max}$ = 100 microns | the height of each of the surface features is (i) ≥10 microns and ≤40 microns, or (ii) ≥10 microns and ≤20 microns |
| $P_{max}$ = 50 microns | (i) $H_{max}$ = 100 microns, or (ii) $H_{max}$ = 40 microns, or (iii) $H_{max}$ = 20 microns, or (iv) $H_{max}$ ≥ 10 microns and ≤100 microns |
| $P_{max}$ = 50 microns | the height of each of the surface features is (i) ≥10 microns and ≤40 microns, or (ii) ≥10 microns and ≤20 microns |
| 10 microns ≤ $P_{max}$ ≤ 100 microns | (i) $H_{max}$ = 100 microns, or (ii) $H_{max}$ = 40 microns, or (iii) $H_{max}$ = 20 microns, or (iv) $H_{max}$ ≥ 10 microns and ≤100 microns |
| 10 microns ≤ $P_{max}$ ≤ 100 microns | the height of each of the surface features is (i) ≥10 microns and ≤40 microns, or (ii) ≥10 microns and ≤20 microns |
| the pitch between each immediately adjacent pair of the surface features is ≥10 microns and ≤50 microns | (i) $H_{max}$ = 100 microns, or (ii) $H_{max}$ = 40 microns, or (iii) $H_{max}$ = 20 microns, or (iv) $H_{max}$ ≥ 10 microns and ≤100 microns |
| the pitch between each immediately adjacent pair of the surface features is ≥10 microns and ≤50 microns | the height of each of the surface features is (i) ≥10 microns and ≤40 microns, or (ii) ≥10 microns and ≤20 microns |

TABLE 1-continued

| Pitch | Height |
|---|---|
| the pitch between each immediately adjacent pair of the surface features is ≥20 microns and ≤50 microns | (i) $H_{max}$ = 100 microns, or (ii) $H_{max}$ = 40 microns, or (iii) $H_{max}$ = 20 microns, or (iv) $H_{max}$ ≥ 10 microns and ≤100 microns |
| the pitch between each immediately adjacent pair of the surface features is ≥20 microns and ≤50 microns | the height of each of the surface features is (i) ≥10 microns and ≤40 microns, or (ii) ≥10 microns and ≤20 microns |
| the pitch between each immediately adjacent pair of the surface features is <100 microns | the height of each of the surface features is <20 microns |
| the pitch between each immediately adjacent pair of the surface features is <30 microns (e.g., ≥10 microns and ≤25 microns) | the height of each of the surface features is <20 microns |
| the pitch between each immediately adjacent pair of the surface features is <100 microns | the height of each of the surface features is ≤15 microns |
| the pitch between each immediately adjacent pair of the surface features is <30 microns (e.g., ≥10 microns and ≤25 microns) | the height of each of the surface features is ≤15 microns |
| the pitch between each immediately adjacent pair of the surface features is <100 microns | the height of each of the surface features is ≤10 microns |
| the pitch between each immediately adjacent pair of the surface features is <30 microns (e.g., ≥10 microns and ≤25 microns) | the height of each of the surface features is ≤10 microns |

As can be seen above, in each of the described embodiments, a maximum height H is specified. One reason that a maximum height H is specified is to limit the possibility that undue deflection/deformation of the tallest surface features (e.g., dome-shaped features 70 (FIG. 3A) and pillars 76 and 70 (FIGS. 3B and 3C)) will occur when contacting surface 64 engages and applies a force to the skin of the user. Too much deflection of the tallest surface features will result in additional static friction during use, and thus is not desirable. Through testing and modeling, the present inventors have determined that a deflection of 1 micron or less in response to a normal pressure of 4.4 kPa and a friction coefficient of 1 is desired in order to avoid undesirable static friction. Thus, in one exemplary embodiment, depending on the particular material that is chosen for seal 38, the maximum height is specified so as to result in surface features that are stiff/rigid enough to have a deflection of 1 micron or less. For example, with such a deflection, the height of each of the surface features may be less than 20 microns, less than or equal to 15 microns, or less than or equal to 10 microns, each with a pitch (e.g., isotropic or anisotropic) of less than 50 microns (or, alternatively a pitch (isotropic or anisotropic) of less than 30 microns). In one particular example, an engineered surface (having anisotropic pitch) was created using a nanosecond laser wherein the surface features have a pitch of 50 microns and a height of 13 microns in a first direction and a pitch of 50 microns and a height of 5 microns in a second direction.

Furthermore, the present inventors have determined that it is beneficial for the engineered surface of contacting portion 64 to prevent excessive "doming" of the user's skin (i.e., deformation of the skin toward the contacting surface 64 when it engages and applies a force to the skin) to an extent where the skin would touch the portions of the contacting surface 64 between the tallest surface features (e.g., bottom surface 72 (FIGS. 3A and 3C) and valleys 78B (FIG. 3B)). Such excessive doming is undesirable because it results in additional skin contact area and thus additional friction and potential red mark formation. Thus, in one exemplary embodiment, it is advantageous to specify a minimum height for the tallest surface features (e.g., dome-shaped features 70 (FIG. 3A) and pillars 76 and 70 (FIGS. 3B and 3C)). Once such embodiment was specified above, wherein, pitch P and height H are characterized as follows: 20 microns≤P≤50 microns and 10 microns≤H≤20 microns.

FIG. 4 is a schematic representation of one particular, non-limiting embodiment of contacting portion 64A having an engineered surface employing the dome-shaped features 70. In this particular embodiment, each dome-shaped feature 70 has an axi-symmetric profile as shown in FIG. 4 such that the dome-shaped feature 70 is symmetrical about a central axis 80 of the dome-shaped feature 70. In addition, each dome-shaped feature 70 includes a hemispherically-shaped tip portion 82 having a radius R that is connected to a frusto-conically-shaped bottom portion 84 (i.e., bottom portion 84 has the shape of a frustum, which as used herein shall mean a cone whose tip has been truncated by a plane parallel to its base) having a half top angle Θ measured with respect to central axis 80. In one particular, exemplary embodiment, tip portion 82 has a radius R that is between 5 and 10 microns. In another particular, exemplary embodiment, which may be combined with the previous embodiment, bottom portion 84 has a half top angle Θ that is equal to 10-60 degrees depending on the material durometer (in one specific implementation it is equal to 30 degrees for a material durometer of 40 Shore A). Furthermore, in still another particular, exemplary embodiment, in addition to the radius R and half top angle Θ parameters just specified, the pitch P and height H of exemplary contacting portion 64 shown in FIG. 4 are characterized as follows: 20 microns≤P≤50 microns and 10 microns≤H≤20 microns.

Moreover, in the exemplary embodiment, contacting portion 64 having an engineered surface as described herein is formed using a molding process, wherein the mold is formed so as to impart the engineered surface onto the molded product. For example, and without limitation, a suitable mold may be constructed by forming the mold surfaces using a laser technology (e.g., a femto-laser, a pico-laser or a nano-laser). Once the mold is formed, the laser engineered mold surface is transferred to the seal 38 to form contacting portion 64. It will be understood, however, that other suitable technologies may also be employed to create a suitable mold, such as, without limitation, milling, polishing, sand blasting, etching or electric discharge machining.

As described elsewhere herein, the sealing elements including an engineered surface that contact the patient's skin may be made of a soft, flexible, cushiony, elastomeric material, such as, without limitation, silicone, an appropriately soft thermoplastic elastomer (such as thermoplastic polyurethanes (TPU)), latex, polybutadiene, a closed cell foam, or any combination of such materials. In addition, such materials may be any rubbery or elastomeric polymer material, e.g., one wherein an organic monomer is selected from the group consisting of butadiene, isoprene, dialkylsiloxanes, diarylsiloxanes, acrylic acid alkyl esters, acrylonitrile, chloroprene, fluorinated ethylene, mixtures of ethylene and vinyl acetate, mixtures of ethylene and one or more acrylic acid esters, and mixtures of ethylene with propylene and a diene. It should be noted that the above listed materials are compatible with the skin. While this is preferred, it is not mandatory and other materials that may not be optimally skin compatible may also be used.

Furthermore, in one or more particular embodiments, any of the materials listed above with the following softness and/or elasticity characteristics may be used to make the sealing elements including an engineered surface described herein: durometer of 2-55 Shore A and elastic modulus of 0.1-3.5 MPa (or 0.1-1.5 MPa), or, alternatively, durometer of 2-50 Shore A and elastic modulus of 0.1-3.5 MPa (or 0.1-1.5 MPa), or, still alternatively, durometer of 5-50 Shore A and elastic modulus of 0.1-3.5 MPa (or 0.1-1.5 MPa). In particular examples, the following specific materials are possible: (i) silicone having durometer of 2 Shore A and an elastic modulus of 0.15 MPa, (ii) silicone having durometer of 5 Shore A and an elastic modulus of 0.3 MPa, and (iii) silicone having durometer of 40 Shore A and an elastic modulus of 1.4 MPa.

As noted elsewhere herein, one benefit of employing contacting portion 64 having an engineered surface is that it provides for a certain degree of self cleaning of seal 38. In particular, it has been determined that, after rubbing against the skin of the user during use, the engineered surfaces as described herein hold less skin cells than a prior art flat reference surface. Because skin organic material that adheres to a mask cushion is a source of bacterial growth, and because such bacterial growth can stimulate skin redness, a configuration that can reduce the number of adhering skin cells will be advantageous.

Figure 5:
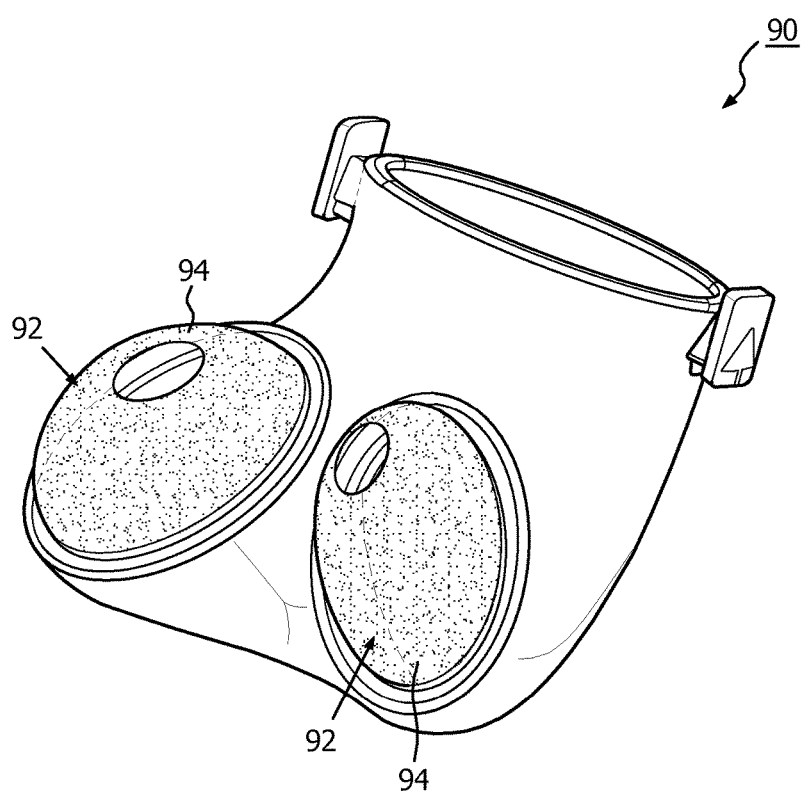
FIG. 5 is an isometric view of an alternative nasal cushion that may be used in a respiratory mask wherein the nasal cushion has an engineered surface as described herein.

While the exemplary embodiments described above employ a contacting surface 64 comprising an engineered surface that is integrally formed with the main body of seal 38, it is to be understood that this is not meant to be limiting and that the contacting surface 64 comprising an engineered surface as described herein may, for example, form part of an in-lay or patch (e.g., disposable) that is coupled to the main body of seal 38 to form seal 38. It is to be further understood that the engineered surfaces as described herein are not limited to use on seal 38, but may be applied to other skin contacting surfaces/components of a patient interface device. For example, an engineered surface as described herein may be employed on forehead pad 46 or other skin contacting components that may be employed with respiratory mask 30, such as cheek pads/supports or chin pads/supports. In addition, engineered surfaces as described herein may be used on contacting portions of different types of patient interface devices, such as, without limitation, the nasal cushion 90 shown in FIG. 5, which includes a pair of laterally spaced dome-shaped nares elements 92. As seen in FIG. 5, each dome-shaped nares elements 92 has a contacting portion 94 having an engineered surface as described herein provided over substantially the entire surface area thereof. It is to be understood that the contacting portions 94 can, alternatively, be provided over only a portion of each nares element 92 in a select pattern or select locations.

As described elsewhere herein, FIG. 4 is a schematic representation of one particular, non-limiting embodiment of contacting portion 64A having an engineered surface employing dome-shaped features 70 wherein each dome-shaped feature 70 has an axi-symmetric profile and is symmetrical about a central axis 80 of the dome-shaped feature 70. In addition, each dome-shaped feature 70 includes a hemispherically-shaped tip portion 82 having a radius R that is connected to a frusto-conically-shaped bottom portion 84.

Figure 6:
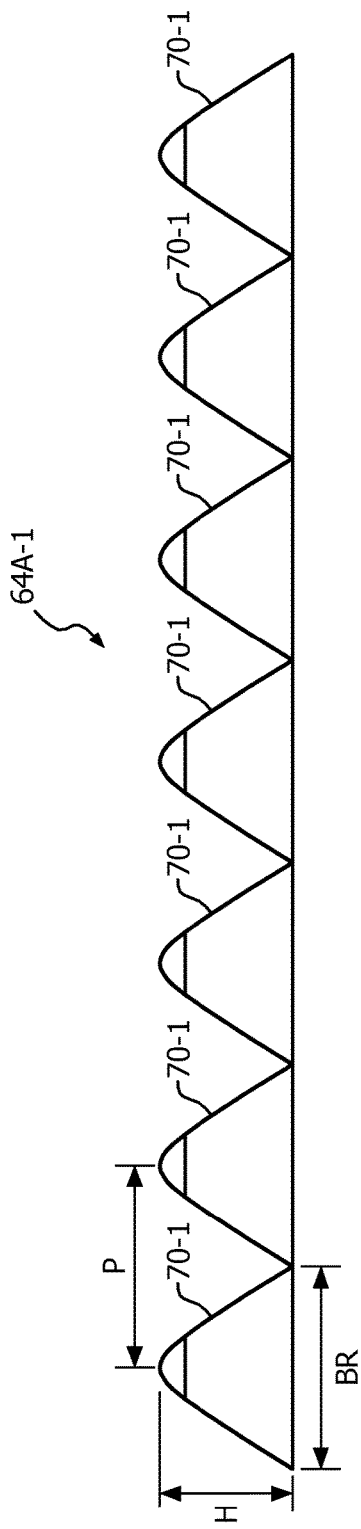

FIG. 6 is a cross-sectional view of a specific, non-limiting implementation of contacting portion 64A of FIG. 4, labeled 64A-1. In contacting portion 64A-1, the engineered surface has the following parameters/characteristics: (i) contacting portion 64A-1 is made of a material, such as silicone, having a durometer of 5 Shore A and an elastic modulus of 0.1-1.5 MPa (e.g. 0.3 MPa), (ii) each dome-shaped feature 70-1 has a base radius (BR) equal to 7.5 microns, (iii) the pitch P of dome-shaped features 70-1 in contacting portion 64A-1 is 15 microns, (iv) the height of each dome-shaped feature 70-1 is 10 microns, and (v) the dome-shaped features 70-1 in contacting portion 64A-1 have a deflection of 1 micron or less (e.g., 0.869926 microns or less) in response to a normal pressure of 0.01 MPa and a friction coefficient of 1.

Figure 7:
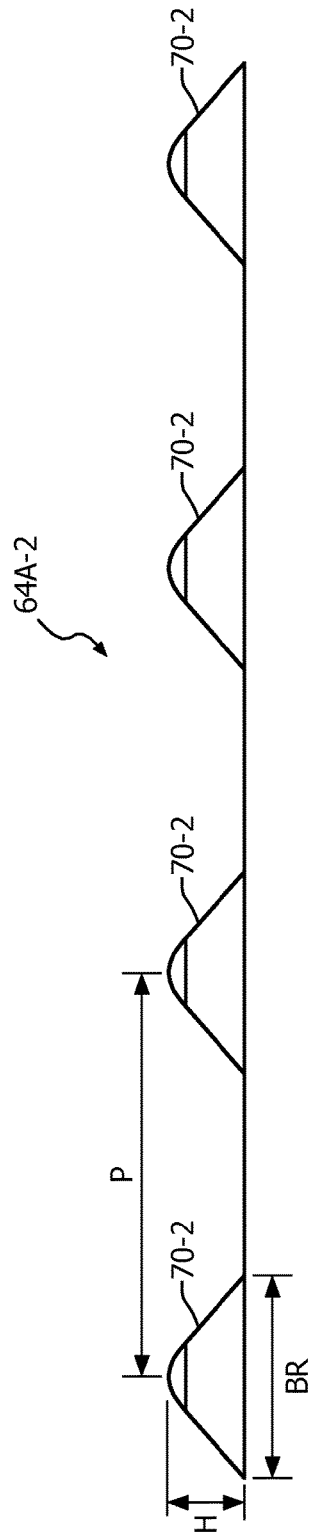

FIG. 7 is a cross-sectional view of another specific, non-limiting implementation of contacting portion 64A of FIG. 4, labeled 64A-2. In contacting portion 64A-2, the engineered surface has the following parameters/characteristics: (i) contacting portion 64A-2 is made of a material, such as silicone, having a durometer of 5 Shore A and an elastic modulus of 0.1-1.5 MPa (e.g. 0.3 MPa), (ii) each dome-shaped feature 70-2 has a base radius (BR) equal to 7.5 microns, (iii) the pitch P of dome-shaped features 70-2 in contacting portion 64A-2 is 30 microns, (iv) the height of each dome-shaped feature 70-2 is 5 microns, and (v) the dome-shaped features 70-2 in contacting portion 64A-2 have a deflection of 0.5 microns or less (e.g, 0.434963 microns or less) in response to a normal pressure of 0.01 MPa and a friction coefficient of 1.

FIG. 8 is a cross-sectional view of yet another specific, non-limiting implementation of contacting portion 64A of FIG. 4, labeled 64A-3. In contacting portion 64A-3, the engineered surface has the following parameters/characteristics: (i) contacting portion 64A-3 is made of a material, such as silicone, having a durometer of 5 Shore A and an elastic modulus of 0.1-1.5 MPa (e.g. 0.3 MPa), (ii) each dome-shaped feature 70-3 has a base radius (BR) equal to 5 microns, (iii) the pitch P of dome-shaped features 70-3 in contacting portion 64A-3 is 15 microns, (iv) the height of each dome-shaped feature 70-3 is 5 microns, and (v) the dome-shaped features 70-3 in contacting portion 64A-3 have a deflection of 0.6 microns or less (e.g., 0.5505 microns or less) in response to a normal pressure of 0.01 MPa and a friction coefficient of 1.

FIG. 9 is a cross-sectional view of still another specific, non-limiting implementation of contacting portion 64A of FIG. 4, labeled 64A-4. In contacting portion 64A-4, the engineered surface has the following parameters/characteristics: (i) contacting portion 64A-4 is made of a material, such as silicone, having a durometer of 5 Shore A and an elastic modulus of 0.1-1.5 MPa (e.g. 0.3 MPa), (ii) each dome-shaped feature 70-4 has a base radius (BR) equal to 5 microns, (iii) the pitch P of dome-shaped features 70-4 in contacting portion 64A-4 is 10 microns, (iv) the height of each dome-shaped feature 70-4 is 5 microns, and (v) the dome-shaped features 70-4 in contacting portion 64A-4 have a deflection of 0.3 microns or less (e.g., 0.244667 microns or less) in response to a normal pressure of 0.01 MPa and a friction coefficient of 1.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A patient interface device, comprising:
  a contacting portion structured to directly engage a user's skin during use of the patient interface device, wherein at least a section of the contacting portion has an engineered surface comprising a plurality of non-random, predesigned surface features each having a like geometry,
  wherein in the section a pitch between each immediately adjacent pair of the surface features is:
    (i) equal, or demonstrates anisotropic pitch such that the pitch between each immediately adjacent pair of the surface features in a first direction is equal to a first pitch value and the pitch between each immediately adjacent pair of the surface features in a second direction transverse to the first direction is equal to a second pitch value different than the first pitch value, and
    (ii) less than or equal to a predetermined maximum pitch value, wherein the predetermined maximum pitch value is greater than or equal to 10 microns and less than or equal to 100 microns, and
  wherein in the section a height of each of the surface features is less than or equal to a predetermined maximum height value.

2. The patient interface device according to claim 1, wherein in the section the height of each of the surface features is equal to one another and less than or equal to the predetermined maximum height value.

3. The patient interface device according to claim 1, wherein the predetermined maximum height value is greater than or equal to 10 microns and less than or equal to 20 microns.

4. The patient interface device according to claim 1, wherein the predetermined maximum height value is any of: (i) 100 microns, (ii) 40 microns, (iii) 20 microns, or (iv) greater than or equal to 10 microns and less than or equal to 100 microns, or wherein the height of each of the surface features is any of: (i) greater than or equal to 10 microns and less than or equal to 40 microns, or (ii) greater than or equal to 10 microns and less than or equal to 20 microns.

5. The patient interface device according to claim 1, wherein the at least a section of the contacting portion including the predesigned surface features is made of a material having a durometer of 2-55 Shore A.

6. The patient interface device according to claim 1, wherein each of the surface features has an axi-symmetric dome-shaped profile.

7. The patient interface device according to claim 6, wherein each of the surface features has a tip portion coupled to a base portion, wherein the tip portion has a radius of between 5 and 10 microns, and wherein the base portion has a half top angle measured with respect to a central axis of the surface feature equal to between 10 and 60 degrees.

8. The patient interface device according to claim 1, wherein the engineered surface comprises a plurality of second surface features, each of the second surface features being a ridge member, each of the surface features being a pillar member formed by an intersection of four adjacent ones of the ridges.

9. The patient interface device according to claim 1, wherein the contacting portion is part of a seal of the patient interface device.

10. The patient interface device according to claim 1, wherein each of the surface features comprises one of the following types of surface features: a bump, a dimple, a pillar, a dome, a valley, a ridge, an undulation or a serration.

11. A method of making a patient interface device, comprising:
  designing an engineered surface wherein at least a section of the engineered surface comprises a plurality of non-random, predesigned surface features each having a like geometry, wherein in the section a pitch between each immediately adjacent pair of the surface features is (i) equal, or demonstrates anisotropic pitch such that the pitch between each immediately adjacent pair of the surface features in a first direction is equal to a first pitch value and the pitch between each immediately adjacent pair of the surface features in a second direction transverse to the first direction is equal to a second pitch value different than the first pitch value, and (ii) less than or equal to a predetermined maximum pitch value, wherein the predetermined maximum pitch value is any of: (i) 50 microns, (ii) 100 microns, or (iii) greater than or equal to 10 microns and less than or equal to 10 microns and less than or equal to 100 microns, or wherein the pitch between each immediately adjacent pair of the surface features is any of: (i) greater than or equal to 10 microns and less than or equal to 50 microns, or (ii) greater than or equal to 20 microns and less than or equal to 50 microns, and wherein in the section a height of each of the surface features is less than or equal to a predetermined maximum height value; and forming a contacting portion for the patient interface device in a manner wherein the contacting portion includes the engineered surface, the contacting portion being structured to directly engage a user's skin.

12. The method according to claim 11, wherein the predetermined maximum height value is any of: (i) 100 microns, (ii) 40 microns, (iii) 20 microns, or (iv) greater than or equal to 10 microns and less than or equal to 100 microns, or wherein the height of each of the surface features is any of: (i) greater than or equal to 10 microns and less than or equal to 40 microns, or (ii) greater than or equal to 10 microns and less than or equal to 20 microns.

13. The patient interface device according to claim 6, wherein in the section the pitch between each immediately adjacent pair of the surface features is 10-30 microns, wherein each of the surface features has a base portion having a radius of 5-7.5 microns, wherein in the section the height of each of the surface features is less than or equal to 10 microns, and wherein a deflection of each of the surface features is equal to 1 micron or less in response to a normal pressure of 0.01 MPa.

14. The patient interface device according to claim 13, wherein the contacting portion is made of a material having a durometer of 5 Shore A and an elastic modulus of 0.1-1.5 MPa.

15. The method according to claim 11, wherein the contacting portion is made of a material having a durometer of 2-55 Shore A.

16. The patient interface device according to claim 1, wherein a deflection of each of the surface features is equal to 1 micron or less in response to a normal pressure of 4.4 kPa.

17. The method according to claim 11, wherein in the section the height of each of the surface features is equal to one another and less than or equal to the predetermined maximum height value.

18. The patient interface device according to claim 1, wherein the pitch between each immediately adjacent pair of the surface features is greater than or equal to 20 microns and less than or equal to 50 microns.

19. The method according to claim 11, wherein the predetermined maximum height value is greater than or equal to 10 microns and less than or equal to 20 microns.

20. The method according to claim 11, wherein the pitch between each immediately adjacent pair of the surface features is greater than or equal to 20 microns and less than or equal to 50 microns.

* * * * *